(12) United States Patent
Anderson et al.

(10) Patent No.: US 6,348,618 B1
(45) Date of Patent: Feb. 19, 2002

(54) BETA-KETOESTER COMPOUNDS

(75) Inventors: Denise Anderson, Zürich; Georg Fráter, Winterthur, both of (CH)

(73) Assignee: Givaudan Roure (International) SA, Geneva (CH)

( * ) Notice: Subject to any disclaimer, the term of this patent is extended or adjusted under 35 U.S.C. 154(b) by 0 days.

(21) Appl. No.: 09/641,656

(22) Filed: Aug. 18, 2000

Related U.S. Application Data

(62) Division of application No. 09/176,291, filed on Oct. 21, 1998, now Pat. No. 6,222,062.

(30) Foreign Application Priority Data

Oct. 21, 1997 (EP) ............................................. 97810783

(51) Int. Cl.$^7$ ............................................... C07C 69/66
(52) U.S. Cl. ...................................................... 560/174
(58) Field of Search ............................ 560/174; 549/262

(56) References Cited

U.S. PATENT DOCUMENTS 5,726,345 A    3/1998  Paget et al.

FOREIGN PATENT DOCUMENTS

| EP | 771 786 | 5/1997 |
| WO | WO 95/04809 | 2/1995 |
| WO | WO 98/07407 | 2/1998 |

OTHER PUBLICATIONS

Benetti, S., et al., *Chem. Reviews*, 95, 1065–1114 (1995).
Kubel, B., *Liebigs Ann. Chem.*, 9, 1392–1401 (1980).
Shimasaki, H., et al., *Chem. Pharm. Bull.*, 43(1), 100–107, (1995).
Parham, W.E., et al., *J. Org. Chem.*, 23, 1705–7, (1958).

*Primary Examiner*—Paul J. Killos
(74) *Attorney, Agent, or Firm*—Bryan Cave, LLP

(57) ABSTRACT

The beta-ketoesters of formula I are useful as precursors for organoleptic compounds, especially for flavors, fragrances and masking agents and antimicrobial compounds.

6 Claims, No Drawings

BETA-KETOESTER COMPOUNDS

This is a divisional of U.S. application Ser. No. 09/176,291, filed Oct. 21, 1998 U.S. Pat. No. 6,222,062.

FIELD OF THE INVENTION

The present invention relates to new beta-keto esters which are useful as precursors for compounds, especially organoleptic compounds, such as flavours, fragrances and masking agents and antimicrobial compounds and insect repellents.

BACKGROUND OF THE INVENTION

A principal strategy currently employed in imparting odours to consumer products is the admixing of the fragrance directly into the product. There are, however, several drawbacks to this strategy. The fragrance material can be too volatile and or too soluble, resulting in fragrance loss during manufacturing, storage, and use. Many fragrance materials are also unstable over time. This again results in loss during storage.

In many consumer products it is desirable for the fragrance to be released slowly over time. Micro-encapsulation and inclusion complexes with cyclodextrins have been used to help decrease volatility, improve stability and provide slow-release properties. However, these methods are for a number of reasons often not successful. In addition, cyclodextrins can be too expensive.

Fragrance precursors for scenting fabrics being washed in the presence of a lipase-containing detergents are described in WO 95/04809. The fragrance precursors contained in the detergent and/or in the softener are cleaved by the lipase and a single odoriferous compound, either an odoriferous alcohol or aldehyde or ketone is yielded. Thereby a prolonged scenting effect on the fabric is obtained.

Beta-amino ester compounds of perfume alcohols and their use as precursors for active alcohols which are released under alkaline conditions are described in the EP-A 0 771 786.

Certain beta-ketoester pro-accords for personal care and personal hygiene articles are disclosed in WO 98/07407.

SUMMARY OF THE INVENTION

The present invention provides beta-keto ester compounds which are useful as precursors for organoleptic compounds, especially for flavours, fragrances and masking agents and antimicrobial compounds.

One object of the present invention is to provide new precursors for compounds with different activities. A further object of the invention is to provide new compounds which are stable under transport and storage conditions. A further object of the present invention is to provide precursor molecules supplying different active compounds simultaneously or successively.

DETAILED DESCRIPTION OF THE INVENTION

The present invention relates to new beta-keto esters of the formula I

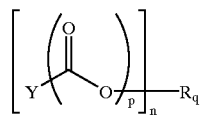

wherein
Y is the residue of an organoleptic ketone or lactone of the formula YH, and if Y is the residue of a cyclic ketone, the carbonyl group may be part of the cyclic structure.
R is H or the residue of a phenol or of a mono- or polyalcohol of the formula R—(OH)$_s$ with s≧1,
p=1, 2
n≧1 and
q=1,2
whereby if n>1 the rests Y may be different or the same with the exception of
3-oxo-5-(2,6,6-trimethyl-cyclohex-1-enyl)-pentanoic acid methyl ester,
3-oxo-5-(2,6,6-trimethyl-cyclohex-2-enyl)-pentanoic acid methyl ester,
3-oxo-5-(2,6,6-trimethyl-cyclohex-1-enyl)-pent-4-enoic acid methyl ester,
3-oxo-2-(2,6,6-trimethyl-cyclohex-1-enylmethyl)-butyric acid ethyl ester,
3-isopropyl-6-methyl-2-oxo-cyclohexane carboxylic acid methyl ester, and
3-isopropyl-6-methyl-2-oxo-cyclohexane carboxylic acid ethyl ester.

The compounds of formula I are not limited to any particular stereoisomers. All possible stereoisomers (E/Z isomers, enantiomers, diastereomers) and all mixtures are thus included within the scope of the invention.

The compounds of formula I are mostly or nearly odourless at room temperature, atmospheric conditions and about 20 to 100% relative humidity. However, under activating conditions, they are cleaved and one or more active compounds with organoleptic and/or antimicrobial properties are generated.

The activating conditions which lead to cleavage and the desired active compounds comprise the presence of skin bacteria, especially axilla bacteria, of an enzyme such as protease or lipase, elevated temperature, acidic or alkaline pH-values or light. Under activating conditions the beta-keto esters of formula I are cleaved into an unstable beta-keto acid and an alcohol or phenol or water (if R=H), then the beta-keto acid decomposes to a ketone or lactone which may be organoleptic according to the following:

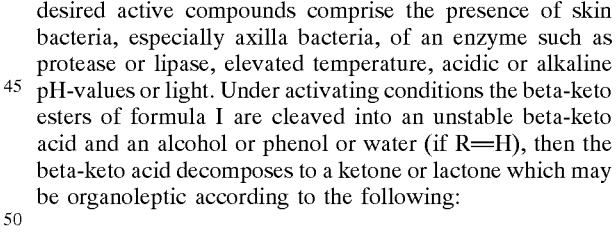

(thereby ROH is an alcohol or phenol which may be organoleptic)

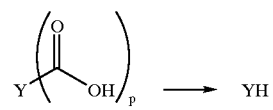

The compounds of formula I, upon cleavage, provide ketones or lactones and/or alcohols or phenols optionally having organoleptic and/or antimicrobial activity and therefore permit the development of useful consumer products with enhanced organoleptic and/or antimicrobial properties. The organoleptic compounds obtained are useful as fragrances, flavours and masking agents and antimicrobial agents. Therefore, the invention also relates to the use of all compounds of formula I as precursors for organoleptic compounds, e.g. flavours, fragrances, masking agents and as precursors for antimicrobial agents.

The beta-keto esters of formula I can act as fragrance precursors in personal care products, in laundry products, cleaning compositions, pet care products and environment scents such as air fresheners. They can also act as precursors for odour masking agents in the same products as the fragrance precursors. They also can act as precursors for antimicrobial agents. Further, they can act as flavour precursors in food and beverage products. The fragrance precursors and the precursors for odour masking agents as well as the flavour precursors of the invention may be used individually in an amount effective to enhance or to mask the characteristic odour or flavour of a material. More commonly, however, the compounds are mixed with other fragrance or flavour components in an amount sufficient to provide the desired odour or flavour characteristics.

Due to the in situ generation of the active compounds the desired effect is prolonged and the substantivity on different substrates is enhanced. If two or more active compounds are provided, they can be generated, depending on the precursor and/or the activating conditions, simultaneously or successively. Further, the precursors of the invention provide slow release of the active compounds.

Compounds of formula I wherein Y is the residue of an organoleptic ketone or lactone are preferred.

Compounds of formula I wherein R=H or the residue of a nonfragrant phenol or of a nonfragrant mono- or polyalcohol, especially having more than 3-C atoms are also preferred.

One preferred group of beta-keto esters of formula I are those in which Y is the residue of a cyclic ketone where the carbonyl group is part of the cyclic structure.

Another preferred group of beta-keto esters of formula I are those in which

Y is a residue of the formula

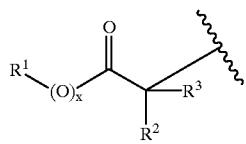

wherein $R^1$ is an aliphatic rest optionally substituted by one or more cycloaliphatic or aromatic rests or $R^1$ is an cycloaliphatic rest optionally substituted by one or more aliphatic rests, $R^2$ is H or an aliphatic rest.

$R^3$ is H or an aliphatic rest and $R^1$, $R^2$ and $R^3$ may be the same or different, x=0 or 1 and when x=1, $R^1$ and $R^2$ together may form an aliphatic ring.

Compounds of formula I may generate the following organoleptic ketones of formula YH:
2-heptyl-cyclopentanone
2,2,6,10-tetramethyltricyclo[5.4.0.0(6, 10)]-undecan-4-one
benzylacetone*
1,2,3,5,6,7-hexahydro-1,1,2,3,3-pentamethyl-4H-inden-4-one*
2,5-dimethyl-oct-2-en-6-one**
2-(butan-2-yl)-cyclohexanone*
2-hexyl-cyclopent-2-en-1-one*
2-(1-methylethyl)-5-methyl-cyclohexanone*
2-(2-methylethyl)-5-methyl-cyclohexanone**
3-methyl-cyclopentadecanone
4-(1,1-dimethylpropyl)pentyl-cyclohexanone*
3-oxo-2-pentyl-cyclopentane-acetic acid methyl ester**
1-(1,2,3,4,5,6,7,8,-octahydro-2,3,8,8-tetramethyl-2-naphthalenyl)-ethanone*
3-methyl-5-propyl-cyclohex-2-en-1-one*
4-(2,6,6-trimethylcyclohex-1-en-1yl)butan-2-one**
4-(2,6,6-trimethylcyclohex-2-en-1-yl)butan-2-one**
2-methyl-5-(1-methylethenyl)-cyclohex-2-en-1-one*
cyclopentadecanone**
1-(4-hydroxyphenyl)-butan-3-one**
4-benzo-1,3-dioxo-5-yl-but-2-one**
4-(1,3-benzodioxol-5-yl)-2-butanone**
nonan-3-one*
nonan-2-one*
octan-2-one*
2-heptanone*
butan-2-one*
6-methyl-hept-5-en-2-one*
6,10-dimethyl-undeca-5,9-dien-2-one*
1-(2,4,4-trimethyl-2-cyclohexen-1-yl)-2-buten-1-one*
carvone**
2-pentyl-cyclopent-2-en-1-one
3-methyl-2-pentyl-cyclopent-2-en-1-one**
2-hexylidenecyclopentanone*
3,5-diethyl-5,6-dimethyl-2-cyclohexenone*
4,4A,5,6,7,8-hexahydro-6-isopropenyl-4,4A-dimethyl-2(3H)-naphthalenone**
3-methyl-6-propylidenecyclohexanone*
4-(1-methylethyl)cyclohex-2-en-1-one
(E)-oct-3-en-2-one
1-(2,3,4,7,8,8A-hexahydro-3,6,8,8-tetramethyl-1H-3A,7-methanoazulen-5-yl)ethanone*
2-hydroxy-3,5-dimethyl-cyclopent-2-en-1-one*
1-(3,3-dimethyl-1-cyclohexen-1-yl)ethanone*
1-(2,4,6-trimethylcyclohex-3-en-1-yl)but-1-en-3-one
acetylisolongifolene
2-(3-methylbut-2-en-1-yl)-3-methyl-cyclopent-2-en-1-one
3-methyl-5-(2,2,3-trimethylcyclopent-3-en-1-yl)pent-3-en-2-one*
5-butylidene-2,2,4-trimethylcyclopentanone
4,4A,5,6,7,8-hexahydro-6-isopropyl-2(3H)-naphthalenone
4-(2,6,6-trimethyl-1-cyclohexen-1-yl)-butan-2-one**
4-methoxyphenylethanone**
acetophenone*
1-(2-naphthalenyl)-ethanone**
3-methyl-4-(2,6,6-trimethyl-2-cyclohexen-1-yl)-3-buten-2-one**
2-acetylpyrazine*
3,5,5-trimethyl-cyclohex-2-en-1,4-dione*
(E)-5-methyl-2-hepten-4-one
dec-3-en-2-one
2-ethyl-3,6,6-trimethylcyclohex-2-enyl-but-2-en-1-one
2,4,4,5,5-pentamethyl-1-cyclopenten-1-yl-ethanone*
whereby * indicates the preferred ketones and ** indicate the more preferred ketones.

Compounds of formula I may generate the following lactones of formula HY:
6-methyl-pyran-2-one
5-heptyl-dihydro-furan-2-one*
5-pentyldihydro-2(3H)-furanone*
5-(3-hexenyl)dihydro-5-methyl-(Z)-2(3H)-furanone 5-hexyldihydro-5-methyl-2(3H)-furanone
5-hexyldihydro-2(3H)-furanone*
5-octyldihydro-2(3H)-furanone
8-(1-methylethyl)-1-oxaspiro[4.5]-decan-2-one*
8-methyl-1-oxaspiro[4.5]-decan-2-one
8-ethyl-1-oxaspiro[4.5]-decan-2-one
5-(1,5-dimethyl-4-hexanyl)dihydro-2(3H)-furanone
2-oxo-5-butyl-tetrahydrofuran*
4-methyl-5-pentyl-dihydro-2(3H)-furan-2-one
5-hexyldihydro-5-methyl-2(3H)-furanone
dihydro-5-methyl-5-vinyl-2(3H)-furanone
octahydro-2H-1-benzopyran-2-one
tetrahydro-6-pentyl-2H-pyran-2-one
tetrahydro-6-hexyl-2H-pyran-2-one
tetrahydro-6-heptyl-2H-pyran-2-one
tetrahydro-6-(3-pentenyl)-(E)-2H-pyran-2-one
tetrahydro-6-(2-pentenyl)-(Z)-2H-pyran-2-one
(E)-oxacycloheptadec-10-en-one**
oxacyclohexadecan-2-one**
dodeca-12-olide
where by * indicates the preferred lactones and ** indicate the more preferred lactones.

Examples of organoleptic monoalcohols and phenols constituting the residue R- in the compounds of formula I and generated upon cleavage are:
amyl alcohol
hexyl alcohol*
2-hexyl alcohol*
heptyl alcohol*
octyl alcohol*
nonyl alcohol*
decyl alcohol*
undecyl alcohol*
lauryl alcohol*
myristic alcohol
3-methyl-but-2-en-1-ol*
3-methyl-1-pentanol
cis-3-hexenol*
cis-4-hexenol*
3,5,5-trimethyl hexanol
3,4,5,6,6-pentamethylheptan-2-ol*
citronellol*
geraniol*
oct-1-en-3-ol
2,5,7-trimethyl octan-3-ol
2-cis-3,7-dimethyl-2,6-octadien-1-ol
6-ethyl-3-methyl-5-octen-1-ol*
3,7-dimethyl-oct-3,6-dienol*
3,7-dimethyloctanol*
7-methoxy-3,7-dimethyl-octan-2-ol *
cis-6-nonenol*
5-ethyl-2-nonanol
6,8-dimethyl-2-nonanol*
2,2,8-trimethyl-7(8)-nonene-3-ol
nona-2,6-dien-1-ol
4-methyl-3-decen-5-ol*
dec-9-en-1-ol
benzylalcohol
2-methyl undecanol
10-undecen-1-ol
1-phenyl ethanol*
2-phenyl ethanol*
2-methyl-3-phenyl-3-propenol
2-phenyl propanol*
3-phenyl propanol*
4-phenyl-2-butanol
2-methyl-5-phenyl pentanol*

2-methyl-4-phenyl-pentanol*
3-methyl-5-phenyl-pentanol*
2-(2-methylphenyl)-ethanol*
4-(1-methylethyl)benzene methanol
4-(4-hydroxyphenyl)butan-2-one*
2-phenoxy ethanol*
4-(1-methylethyl)-2-hydroxy-1-methyl benzene
2-methoxy-4-methyl phenol
4-methyl phenol
anisic alcohol*
p-tolyl alcohol*
cinnamic alcohol*
vanillin*
ethyl vanillin*
eugenol*
isoeugenol*
thymol
anethol*
decahydro 2-naphthalenol
borneol*
cedrenol*
farnesol*
fenchyl alcohol*
menthol*
3,7,11-trimethyl-2,6,10-dodecatrien-1-ol
alpha ionol*
tetrahydro ionol*
2-(1,1-dimethylethyl)cyclohexanol*
3-(1,1-dimethylethyl)cyclohexanol*
4-(1,1-dimethylethyl)cyclohexanol*
4-isopropyl cyclohexanol
6,6-dimethyl-bicyclo[3.3.1]hept-2-ene-2-ethanol
6,6-dimethyl-bicyclo[3.1.1]hept-2-ene-methanol*
p-menth-8-en-3-ol*
3,3,5-trimethyl cyclohexanol
2,4,6-trimethyl-3-cyclohexenyl-methanol*
4-(1-methylethyl)cyclohexyl-methanol*
4-(1,1-dimethylethyl)cyclohexanol
2-(1,1-dimethylethyl)cyclohexanol
2,2,6-trimethyl-alpha-propyl cyclohexane propanol*
5-(2,2,3-trimethyl-3-cyclopentenyl)-3-methylpentan-2-ol*
3-methyl-5-(2,2,3-trimethylcyclopent-3-enyl)pent-4-en-2-ol*
2-ethyl-4(2,2,3-trimethylcyclopent-3-en-1-yl)but-2-en-1-ol*
4-(5,5,6-trimethylbicyclo[2.2.1]hept-2-yl)-cyclohexanol*
2-(2-methylpropyl)-4-hydroxy-4-methyl-tetrahydropyran*
2-cyclohexyl propanol*
2-(1,1-dimethylethyl)-4-methyl cyclohexanol*
1-(2-tert-butyl-cyclohexyloxy)-2-butanol*
1-(4-isopropyl-cyclohexyl)-ethanol*
2,6-dimethyl-oct-7-en-2-ol**
2,6-dimethyl-heptan-2-ol**
3,7-dimethyl-octa-1,6-dien-3-ol**
whereby * indicates the preferred organoleptic alcohols and phenols and ** indicate the more preferred organoleptic alcohols and phenols.

Examples of preferred non-organoleptic alcohols and phenols constituting the residue R- in the compounds of formula I are:
serine
tyrosine
threonine
7-hydroxy-4-methyl coumarin
benzyldimethyl-2-hydroxyethylammonium chloride
[polyoxyethylene (4) lauryl ether]
[polyoxyethylene (2) cetyl ether]

[polyoxyethylene (2) stearyl ether]

Other preferred non-organoleptic alcohols and phenols are those with an affinity to fibers or those used in cosmetics and laundry formulations. A list of suitable cosmetic alcohols and phenols can be found in the Cosmetic Ingredient Handbook edited by Joanne M. Nikitakis. Suitable surfactant alcohols can be found e.g. in Surfactants Europe edited by Gordon L. Hollis. Examples of alcohols and phenols with special affinity to fibers are those that contain one or more quaternary amine groups or silicon atoms.

Examples of polyalcohols constituting the residue R- in the compounds of formula I are: diols such as: diethylene glycol, propylene glycol, triethylene glycol, 4,4'-bicyclohexyldiol, N,N'-bis-(2-hydroxyethyl) ethylenediamine, 1,3-bis-(4-hydroxybutyl)-1,1,3,3-tetramethyl-disiloxane, 1,4-bis-(hydroxymethyl)-cyclohexane triols such as: glycerol, cis,cis-1,3,5-cyclohexanetriol, triethanolamine sugars such as: furanoside and pyranoside sugars such as glucose, fructose polymers such as: hydroxyethylcellulose, hydroxypropylcellulose.

It is a matter of course, that it is not possible to give a complete list of the organoleptic and/or antimicrobial ketones, lactones, alcohols and phenols and non-organoleptic, especially nonfragrant alcohols, phenols and polymeric alcohols which are generated as a result of the desired cleavage of the beta-keto esters of formula I by skin bacteria, by enzymes, by elevated temperatures or by acidic and/or alkaline pH-values. The skilled person is, however, quite aware of those ketones, lactones, alcohols and phenols which provide the desired organoleptic, e.g. fragrance, flavour and odour masking and/or antimicrobial effects.

The compounds of formula I may preferably be used as sustained release odorants and flavours but also to mask or attenuate undesirable odours or to provide additional odours not initially present in consumer products, i.e. personal care products such as cosmetic products destined for application to human skin such as underarm deodorants or antiperspirants or other deodorants contacting the body, or in hand lotions, hair care products such as shampoos and conditioners, baby powders, baby lotions, ointments, foot products, facial cleansers, body wipes, facial makeup, colognes, after-shave lotions, shaving creams, etc. Additional applications include laundry detergents, fabric softeners, fabric softener sheets, (automatic) dishwasher detergents and all purpose cleaners. Further applications are air fresheners and odorants, odour masking agents and/or antimicrobial agents.

The compounds I are also useful in the flavouring and aromatizing of cooked foods. Addition of the beta-keto esters either singly or as a mixture to a cake batter, e.g. a microwave cake batter, serves to impart appropriate baking aromas to the cake as it is heated in the microwave as well as impart flavouring in the finished product. Compounds I are also useful in the flavouring and aromatizing of beverages, e.g. hot beverages such as teas and instant beverages prepared by adding hot water to a powder. Compounds I can also act as slow release agents in acidic or alkaline beverages. Further, these compounds are also useful for flavouring and aromatizing tobacco products, e.g. cigarettes.

The amount required to produce the desired, overall effect varies depending upon the particular compounds of formula I chosen, the product in which it will be used, and the particular effect desired.

For example, depending upon the selection and concentration of the compound chosen, when a compound of the formula I is added either singly or as a mixture, e.g. to a deodorant or laundry product composition at levels ranging from about 0.1 to about 10% by weight, or most preferred about 0.25 to about 4% by weight, an odorant, i.e. at least one odoriferous ketone, lactone, alcohol or phenol in an "organoleptically effective amount" is released when the product is used. This newly formed odorant serves to enhance the odour of the product itself or of a fragrance present in the product.

Depending upon the selection and concentration, addition of the compounds I, either singly or as a mixture, to cigarette tobacco at levels ranging from about 5 ppm to about 50,000 ppm tends to enhance the smoking flavour and/or mask undesirable smoking odours. An important property of these compounds I is that the flavourant or odorant is covalently bound as a non-volatile compound and the flavourant or odorant is released only when the tobacco product is ignited and bums.

Addition of the compounds of formula I either separately or as a mixture at levels suitably ranging from about 5 ppm to about 50,000 ppm by weight onto the media enclosing the tobacco serves to incorporate the odorant/flavourant in the side-stream smoke of the tobacco. Air borne flavourants and/or odorants are thus introduced. This newly formed odorant or flavourant serves to enhance or mask the smoking odours depending upon selection and use levels of the compounds I.

As is evident from the above compilation of ketones, lactones, alcohols and phenols, a broad range of known odorants or flavours or mixtures can be generated from precursors of the invention. While manufacturing compositions the precursors of the invention may be used according to methods known to the perfumer, such as e.g. from W. A. Poucher, Perfumes, Cosmetics, Soaps, 2, 7th Edition, Chapman and Hall, London 1974.

The compounds of formula I can be prepared by using standard methods known to the skilled chemist. A wide variety of methods for their preparation is known. One example for this knowledge is Chem.Rev. (1995), 1065–1114.

Convenient methods are outlined in the Examples without limiting the invention thereto.

EXAMPLE 1

5-Heptyl-2-oxo-tetrahydro-furan-3-carboxylic acid methylester

To a mixture of 203 g 5-heptyl-dihydro-furan-2-one and 390 g dimethylcarbonate was slowly added 40 g of sodium hydride. The temperature increased to 65° C. After the temperature returned to room temperature, the reaction mixture was poured into saturated citric acid and extracted with hexane. The organic layer was dried and evaporated to dryness. The residue was distilled to yield 150.5 g of a colourless liquid.

| | |
|---|---|
| NMR (CDCl$_3$) | 4.75–4.36 (m, 1H); 3.8 (d, 3H); 3.68–3.55 (m, 1H); 2.8–2.45 (m, 1H); 2.45–2.0 (m, 1H); 1.96–1.08 (m, 12H); 0.89 (t, 3H) |

EXAMPLE 2

5-Heptyl-2-oxo-tetrahydro-furan-3-carboxylic acid ethylester

According to the procedure of Example 1, 5-heptyl-2-oxo-tetrahydro-furan-3-carboxylic acid ethyl ester was prepared from 5-heptyl-dihydro-furan-2-one, diethyl carbonate and sodium hydride.

EXAMPLE 3

3-Oxo-5-(2,6,6-trimethyl-cyclohex-2-enyl)-pentanoic acid methyl ester

According to the procedure of Example 1, 3-oxo-5-(2,6,6-trimethyl-cyclohex-2-enyl)-pentanoic acid methyl ester was prepared from 4-(2,6,6-trimethylcyclohex-2-en-1-yl) butan-2-one, dimethyl carbonate and sodium hydride.

EXAMPLE 4

3-Oxo-5-(2,6,6-trimethyl-cyclohex-1-enyl)-pentanoic acid methyl ester

According to the procedure of Example 1, 3-oxo-5-(2,6,6-trimethyl-cyclohex-1-enyl)-pentanoic acid methyl ester was prepared from 4-(2,6,6-trimethylcyclohex-1-en-1-yl) butan-2-one, dimethyl carbonate and sodium hydride.

EXAMPLE 5

2,4,7-Trimethyl-3-oxo-oct-6-enoic acid methyl ester

According to the procedure of Example 1, 2,4,7-trimethyl-3-oxo-oct-6-enoic acid methyl ester was prepared from 2,5-dimethyl-oct-2-en-6-one, dimethyl carbonate and sodium hydride.

EXAMPLE 6

2,4,7-Trimethyl-3-oxo-oct-6-enoic acid ethyl ester

According to the procedure of Example 1, 2,4,7-trimethyl-3-oxo-oct-6-enoic acid ethyl ester was prepared from 2,5-dimethyl-oct-2-en-6-one, diethyl carbonate and sodium hydride.

EXAMPLE 7

3-Isopropyl-6-methyl-2-oxo-cyclohexanecarboxylic acid methyl ester

According to the procedure of Example 1, 3-isopropyl-6-methyl-2-oxo-cyclohexanecarboxylic acid methyl ester was prepared from 2-(2-methylethyl)-5-methyl-cyclohexanone, dimethyl carbonate and sodium hydride.

EXAMPLE 8

6-Isopropenyl-3-methyl-2-oxo-cyclohex-3-ene-carboxylic acid ethyl ester

According to the procedure of Example 1, 6-isopropenyl-3-methyl-2-oxo-cyclohex-3-ene-carboxylic acid ethyl ester was prepared from 2-methyl-5-(1-methylethenyl)-cyclohex-2-en-1-one, diethyl carbonate and sodium hydride.

EXAMPLE 9

3-Oxo-5-(2,6,6-trimethyl-cyclohex-1-enyl)-pent-4-enoic acid methyl ester

According to the procedure of Example 1, 3-oxo-5-(2,6,6-trimethyl-cyclohex-1-enyl)-pent-4-enoic acid methyl ester was prepared from 4-(2,6,6-trimethylcyclohex-1-en-1-yl)-but-3-en-2-one, dimethyl carbonate and sodium hydride.

EXAMPLE 10

2-Oxo-cyclopentanepentacarboxylic acid ethyl ester

According to the procedure of Example 1, 2-oxo-cyclopentadecanecarboxylic acid ethyl ester was prepared from cyclopentadecanone, diethyl carbonate and sodium hydride.

EXAMPLE 11

3-Oxo-5-(2,6,6-trimethyl-cyclohex-1-enyl)-pentanoic acid ethyl ester

According to the procedure of Example 1, 3-oxo-5-(2,6,6-trimethyl-cyclohex-1-enyl)-pentanoic acid ethyl ester was prepared from 4-(2,6,6-trimethylcyclohex-1-en-1-yl)butan-2-one, diethyl carbonate and sodium hydride.

EXAMPLE 12

3-(4-Methoxy-phenyl)-3-oxo-propionic acid ethyl ester

According to the procedure of Example 1, 3-(4-methoxy-phenyl)-3-oxo-propionic acid ethyl ester was prepared from 4-methoxyphenyl ethanone, diethyl carbonate and sodium hydride.

EXAMPLE 13

3-(4-Methoxy-phenyl)-3-oxo-propionic acid methyl ester

According to the procedure of Example 1, 3-(4-methoxy-phenyl)-3-oxo-propionic acid methyl ester was prepared from 4-methoxyphenyl ethanone, dimethyl carbonate and sodium hydride.

EXAMPLE 14

3-Oxo-3-pyrazin-2-yl-propionic acid ethyl ester

According to the procedure of Example 1, 3-oxo-3-pyrazin-2-yl-propionic acid ethyl ester was prepared from 2-acetylpyrazine, diethyl carbonate and sodium hydride.

EXAMPLE 15

3-Oxo-nonanoic acid ethyl ester

According to the procedure of Example 1, 3-oxo-nonanoic acid ethyl ester was prepared from octan-2-one, diethyl carbonate and sodium hydride.

EXAMPLE 16

2-(5,5-Dimethyl-cyclohex-1-enecarbonyl)-pent-4-enoic acid ethyl ester

According to the procedure of Example 1, 2-(5,5-dimethyl-cyclohex-1-enecarbonyl)-pent-4-enoic acid ethyl ester was prepared from 1-(5,5-dimethyl-1-(6)-cyclohexen-1-yl)-4-penten-1-one, diethyl carbonate and sodium hydride.

EXAMPLE 17

7-Methyl-3-oxo-oct-6-enoic acid ethyl ester

According to the procedure of Example 1, 7-methyl-3-oxo-oct-6-enoic acid ethyl ester was prepared from 6-methyl-hept-5-en-2-one, diethyl carbonate and sodium hydride.

EXAMPLE 18

7-Methyl-3-oxo-oct-6-enoic acid methyl ester

According to the procedure of Example 1, 7-methyl-3-oxo-oct-6-enoic acid methyl ester was prepared from 6-methyl-hept-5-en-2-one, dimethyl carbonate and sodium hydride.

EXAMPLE 19

3-Isopropyl-6-methyl-2-oxo-cyclohexanecarboxylic acid ethyl ester

According to the procedure of Example 1, 3-isopropyl-6-methyl-2-oxo-cyclohexanecarboxylic acid ethyl ester was prepared from 2-(2-methylethyl)-5-methyl-cyclohexanone, diethyl carbonate and sodium hydride.

EXAMPLE 20

2,4,7-Trimethyl-3-oxo-oct-6-enoic acid tert-butyl ester

To a mixture of 6.8 g 60% sodium hydride and 30.0 g carbonic acid di-tert-butyl ester (Parham, Loew, J.Org.Chem., 23 (1958), 1705–1707) in 200 ml of THF, 13.11 g dimethyloctenone was dropped in at reflux. To start the reaction, a catalytic amount of potassium hydride (20%) and sodium methylate was added. The reaction mixture was then stirred 3 days at reflux. Then it was cooled to room temperature and quenched with tert-butanol. The mixture was extracted with ether and the organic phase was washed with water, dried, filtered and evaporated to dryness. The resulting yellow oil was purified by chromatography to yield 2.90 g of a colourless oil.

| | |
|---|---|
| NMR (CDCl$_3$)δ | 5.13–4.98 (t, 1H), 3.68–3.47 (m, 1H), 2.90–2.66 (m, 1H), 2.45–1.95 (m, 2H), 1.73–1.55 (m, 6H), 1.44 (s, 9H), 1.33–1.19 (m, 3H), 1.16–1.02 (d, 3H). |

EXAMPLE 21

2-Benzo[1,3]dioxol-5-ylmethyl-3-oxo-butyric acid ethyl ester

To a solution of 117.2 g sodium iodide in 700 ml of acetonitrile, first 85.9 g trimethylchlorosilane and then 20.56 g ethyl acetoacetate were dropped in at room temperature. After cooling down to 0–5° C., a solution of 23.65 g Piperonal in 50 ml of acetonitrile was dropped in. Then the mixture was stirred at room temperature for 5 hours and then at 60° C. overnight. After the mixture was cooled down to room temperature it was diluted with ether and water. The organic phase was separated and washed with saturated sodium thiosulfate until the color of the iodine was gone. Then the organic phase was washed with water, dried, filtered and evaporated to dryness. The resulting dark oil was purified by chromatography to yield 13.7 g of a yellow oil.

| | |
|---|---|
| NMR (CDCl$_3$)δ | 6.81–6.65 (m, 3H), 5.91 (s, 2H), 4.27–4.07 (q, 2H), 3.80–3.66 (t, 1H), 3.13–3.01 (d, 2H), 2.19 (s, 3H), 1.30–1.17 (t, 3H). |

EXAMPLE 22

2-Benzyl-3-oxo-butyric acid ethyl ester

To a suspension of 36.08 g 60% sodium hydride in 1000 ml of toluene, 112.9 g ethyl acetoacetate was dropped in. The temperature rose to 60° C. and then the reaction mixture was stirred for 1 hour at room temperature. Then 17.54 g Aliquat 336 were added and the reaction mixture was heated to 84° C. Now a solution of 54.90 g benzyl chloride in 50 ml of toluene was dropped in. Then the mixture was stirred at 84° C. for 26 hours. After the mixture was cooled down to room temperature, it was acidified with 250 ml of 2N HCl and extracted with ether. The combined organic phase was washed with 5% sodium bicarbonate and brine, dried, filtered and evaporated to dryness. The resulting brown oil was purified by chromatography to yield 55.74 g of a colourless oil.

| | |
|---|---|
| NMR (CDCl$_3$)δ | 7.38–7.11 (m, 5H), 4.25–4.07 (q, 2H), 3.85–3.71 (t, 1H), 3.21–3.10 (d, 2H), 2.19 (s, 3H), 1.28–1.12 (t, 3H). |

EXAMPLE 23

2-Benzyl-3-oxo-butyric acid methyl ester

According to the procedure of Example 22, 2-benzyl-3-oxo-butyric acid methyl ester was prepared from methyl acetoacetate, benzyl chloride, sodium hydride and Aliquat 336.

EXAMPLE 24

2-(4-Hydroxy-benzyl)-3-oxo-butyric acid ethyl ester

According to the procedure of Liebigs Ann. Chem. (1980), 9, 1392, 2-(4-hydroxy-benzyl)-3-oxo-butyric acid ethyl ester was prepared from 2-acetyl-3-(4-hydroxy-phenyl)-acrylic acid ethyl ester, Raney-nickel, hydrogen.

EXAMPLE 25

2-Acetyl-5-methyl-hex-4-enoic acid ethyl ester

To a solution of 26.05 g ethyl acetoacetate in 150 ml of dimethylformamide, 8.30 g 60% sodium hydride were added portionwise over 1 hour while the temperature rose to 60° C. After cooling down to room temperature, a solution of 24.8 g 1-chloro-3-methyl-2-butene in 50 ml of dimethylformamide was dropped in. Then the mixture was stirred at room temperature for 2.5 hours. The mixture was quenched with water and extracted with ether. The combined organic phase was dried, filtered and evaporated to dryness. The resulting yellow oil was purified by distillation to yield 23.16 g of a colourless oil.

| | |
|---|---|
| NMR (CDCl$_3$)δ | 5.11–4.96 (m, 1H), 4.29–4.11 (q, 2H), 3.49–3.36 (t, 1H), 2.62–2.47 (t, 2H), 2.22 (s, 3H), 1.78–1.59 (2s, 6H), 1.35–1.19 (t, 3H). |

EXAMPLE 26

2-Propionyl-heptanoic acid ethyl ester

According to the procedure of Example 25, 2-propionyl-heptanoic acid ethyl ester was prepared from 3-oxo-pentanoic acid ethyl ester, 1-bromopentane and sodium hydride.

EXAMPLE 27

2-Acetyl-hexanoic acid methyl ester

According to the procedure of Example 25, 2-acetyl-hexanoic acid methyl ester was prepared from methyl acetoacetate, 1-chlorobutane and sodium hydride.

EXAMPLE 28

2-Acetyl-heptanoic acid methyl ester

According to the procedure of Example 25, 2-acetyl-heptanoic acid methyl ester was prepared from methyl acetoacetate, 1-chloropentane and sodium hydride.

EXAMPLE 29

2-Acetyl-octanoic acid methyl ester

According to the procedure of Example 25, 2-acetyl-octanoic acid methyl ester was prepared from methyl acetoacetate, 1-chlorohexane and sodium hydride.

EXAMPLE 30

2-Acetyl-octanoic acid ethyl ester

According to the procedure of Example 25, 2-acetyl-octanoic acid ethyl ester was prepared from ethyl acetoacetate, 1-chlorohexane and sodium hydride.

EXAMPLE 31

5-Heptyl-2-oxo-tetrahydro-furan-3-carboxylic acid phenethyl ester

A mixture of 24.2 g 5-heptyl-2-oxo-tetrahydro-furan-3-carboxylic acid methyl ester, 24.4 g phenylethyl alcohol and 1.4 g tetraisopropyl-ortho-titanate was heated under nitrogen atmosphere to 130° C. for 5 minutes while methanol was distilled off. Then the reaction mixture was cooled to room temperature, poured into water and extracted with hexane. The organic layer was dried and evaporated to dryness. The residue was chromatographed to yield 23.9 g of a slightly yellow oil.

NMR (CDCl3) 7.4–7.15 (m, 5H); 4.5–4.3 (m, 2H); 3.62–3.5 (m, 1H); 3.08–2.91 (m, 2H); 2.65–2.4 (m, 1H); 2.34–1.96 (m, 1H) 1.88–1.11 (m, 13H); 0.9 (t, 3H)

EXAMPLE 32

5-Heptyl-2-oxo-tetrahydro-furan-3-carboxylic acid 3,7-dimethyl-oct-6-enyl ester

According to the procedure of Example 31, 5-heptyl-2-oxo-tetrahydro-furan-3-carboxylic acid 3,7-dimethyl-oct-6-enyl ester was prepared from 5-heptyl-2-oxo-tetrahydro-furan-3-carboxylic acid methyl ester, 3,7-dimethyl-oct-6-en-1-ol and tetraisopropyl-ortho-titanate.

EXAMPLE 33

5-Heptyl-2-oxo-tetrahydro-furan-3-carboxylic acid 3,7-dimethyl-octa-2,6-dienyl ester According to the procedure of Example 31, 5-heptyl-2-oxo-tetrahydro-furan-3-carboxylic acid 3,7-dimethyl-octa-2,6-dienyl ester was prepared from 5-heptyl-2-oxo-tetrahydro-furan-3-carboxylic acid methyl ester, 3,7-dimethyl-octa-2,6-dien-1-ol and tetraisopropyl-ortho-titanate.

EXAMPLE 34

5-Heptyl-2-oxo-tetrahydro-furan-3-carboxylic acid 2-phenoxy-ethyl ester

According to the procedure of Example 31, 5-heptyl-2-oxo-tetrahydro-furan-3-carboxylic acid 2-phenoxy-ethyl ester was prepared from 5-heptyl-2-oxo-tetrahydro-furan-3-carboxylic acid methyl ester, 2-phenoxyethanol, and tetraisopropyl-ortho-titanate.

EXAMPLE 35

2-Oxo-cyclopentadecanecarboxylic acid hex-3-enyl ester

According to the procedure of Example 31, 2-oxo-cyclopentadecanecarboxylic acid hex-3-enyl ester was prepared from 2-oxo-cyclopentadecanecarboxylic acid ethyl ester, cis-3-hexenol and tetraisopropyl-ortho-titanate.

EXAMPLE 36

2-Oxo-cyclopentadecanecarboxylic acid 3,7-dimethyl-octa-2,6-dienyl ester

According to the procedure of Example 31, 2-oxo-cyclopentadecanecarboxylic acid 3,7-dimethyl-octa-2,6-dienyl ester was prepared from 2-oxo-cyclopentadecanecarboxylic acid ethyl ester and tetraisopropyl-ortho-titanate.

EXAMPLE 37

3-Oxo-5-(2,6,6-trimethyl-cyclohex-2-enyl)-pentanoic acid 2-[3-oxo-5-(2,6,6-trimethyl-cyclohex-2-enyl)-pentanoyloxy]-ethyl ester A mixture of 25.2 g 3-oxo-5-(2,6,6-trimethyl-cyclohex-2-enyl)-pentanoic acid methyl ester and 4.3 g ethylene glycol was slowly heated to 180° C. while distilling off methanol. On completion, the reaction mixture was chromatographed over silica gel to yield a colourless liquid.

NMR (CDCl$_3$) 5.35 (s, 2H); 4.37 (s, 4H); 3.48 (s, 4H); 2.55 (t, 4H); 2.05–1.86 (m, 4H); 1.68 (m, 6H); 1.56–1.06 (m, 10H); 0.91 (s, 6H); 0.87 (s, 6H).

EXAMPLE 38

3-Oxo-5-(2,6,6-trimethyl-cyclohex-1-enyl)-pent-4-enoic acid 2-[3-oxo-5-(2,6,6-trimethyl-cyclohex-1-enyl)-pent-4-enoyloxy]-ethyl ester According to the procedure of Example 37, 3-oxo-5-(2,6,6-trimethyl-cyclohex-1-enyl)-pent-4-enoic acid 2-[3-oxo-5-(2,6,6-trimethyl-cyclohex-1-enyl)-pent-4-enoyloxy]-ethyl ester was prepared from 3-oxo-5-(2,6,6-trimethyl-cyclohex-1-enyl)-pent-4-enoic acid methyl ester and ethylene glycol.

EXAMPLE 39

5-Heptyl-2-oxo-tetrahydro-furan-3-carboxylic acid 2-(5-heptyl-2-oxo-tetrahydro-furan-3-ylcarbonyloxy)-ethyl ester According to the procedure of Example 37, 5-heptyl-2-oxo-tetrahydro-furan-3-carboxylic acid 2-(5-heptyl-2-oxo-tetrahydro-furan-3-ylcarbonyloxy)-ethyl ester was prepared from 5-heptyl-2-oxo-tetrahydro-furan-3-carboxylic acid methyl ester and ethylene glycol.

EXAMPLE 40

Malonic acid didec-9-enyl ester

To a mixture of 150 g dimethyl malonate and 464 g dec-9-en-1-ol, 30 g sodium methoxide (5.4 M in methanol)

was dropped in. The mixture was heated to 120° C. to and the methanol formed was distilled off. After 6 hours, the mixture was cooled down, diluted with ether and washed with HCl 2N, saturated sodium bicarbonate and water. The organic phase was dried, filtered and evaporated to dryness. The resulting yellow oil was purified by distillation to yield 258 g of a yellow oil.

NMR (CDCl$_3$)δ  5.93–5.68 (m, 2H), 5.08–4.87 (m, 4H), 4.21–4.05 (t, 4H), 3.37 (s, 2H), 2.14–1.92 (m, 4H), 1.81–1.51 (m, 4H), 1.50–1.18 (m, 20H).

EXAMPLE 41

Malonic acid dihex-3-enyl ester

According to the procedure of Example 40, malonic acid dihex-3-enyl ester was prepared from dimethyl malonate, cis-3-hexenol and sodium methoxide.

EXAMPLE 42

Malonic acid bis-(3,7-dimethyl-oct-6-enyl) ester

According to the procedure of Example 40, malonic acid bis-(3,7-dimethyl-oct-6-enyl) ester was prepared from dimethyl malonate, citronellol and sodium methoxide.

EXAMPLE 43

Succinic acid mono-(3,7-dimethyl-oct-6-enyl) ester

A solution of 30.0 g succinic anhydride, 46.9 g citronellol, 36.0 g pyridine and 2.2 g 4-dimethylaminopyridine in 300 ml of dichloromethane was refluxed for 22 hours. Then the solution was cooled, ether was added and the organic phase was washed with 2N HCl and water to neutrality, dried and evaporated to dryness. The residue was wipe-film distilled to yield 36.4 g of a colourless liquid.

NMR (CDCl$_3$)  d10.0 (s, 1H), 5.08 (t, 1H), 4.13 (t, 2H), 2.75–2.54 (m, 4H), 2.08–1.88 (m, 2H), 1.69 (s, 3H), 1.60 (s, 3H), 1.80–1.00 (m, 5H), 0.91 (d, 3H) ppm.

EXAMPLE 44

3-Chlorocarbonyl-propionic acid 3,7-dimethyl-oct-6-enylester

A solution of 35.5 g succinic acid mono-(3,7-dimethyl-oct-6-enyl) ester and 12.3 g pyridine in 200 ml of ether was cooled in an ice bath. Then a solution of 18.0 g thionyl chloride in 100 ml of ether was added dropwise at 5–10° C. during 90 min. The resulting solution was stirred overnight at room temperature, then it was filtered and evaporated to dryness. The residue was not further purified to yield 31.5 g of a yellow liquid.

NMR (CDCl$_3$)  d5.08 (t, 1H), 4.13 (t, 2H), 3.21 (t, 2H), 2.64 (t, 3H), 2.10–1.87 (m, 2H), 1.68 (s, 3H), 1.60 (s, 3H), 1.80–1.05 (m, 5H), 0.91 (d, 3H) ppm.

EXAMPLE 45

2-[3-(2,6,6-Trimethyl-cyclohex-1-enyl)-acryloyl]-malonic acid dihex-3-enyl ester To a suspension of 2.10 g 60% sodium hydride in 20 ml of THF, a solution of 14.00 g malonic acid dihex-3-enyl ester in 20 ml of THF were dropped in at 0–5° C. The reaction mixture was stirred 1 hour at room temperature. Then a solution of 11.9 g 3-(2,6,6-trimethyl-cyclohex-1-enyl)-acryloyl chloride (Shimasaki et al., Chem. Pharm. Bull., 43 (1995) 1, 100–107) in 40 ml of THF was dropped in and the reaction mixture was stirred at room temperature for 21 hours. Then the reaction mixture was diluted with ether and the organic phase was washed with water, dried, filtered and evaporated to dryness. The resulting yellow oil was purified by chromatography to yield 4.22 g of a yellow oil.

NMR (CDCl$_3$)δ  7.52–7.30 (m, 1H), 6.47–6.22 (m, 1H), 5.61–5.19 (m, 4H), 4.29–4.11 (q, 4H), 2.53–2.32 (m, 4H), 2.17–1.92 (m, 6H), 1.79 (s, 3H), 1.71–1.41 (m, 5H), 1.08 (s, 6H), 1.02–0.89 (t, 6H).

EXAMPLE 46

2-[3-(2,6,6-Trimethyl-cyclohex-1-enyl)-acryloyl]-malonic acid didec-9-enyl ester According to the procedure of Example 45, 2-[3-(2,6,6-trimethyl-cyclohex-1-enyl)-acryloyl]-malonic acid didec-9-enyl ester was prepared from malonic acid didec-9-enyl ester, 3-(2,6,6-trimethyl-cyclohex-1-enyl)-acryloyl chloride (Shimasaki et al., Chem. Pharm. Bull., 43 (1995) 1, 100–107) and sodium hydride.

EXAMPLE 47

2-[3-(2,6,6-Trimethyl-cyclohex-1-enyl)-acryloyl]-malonic acid bis-(3,7-dimethyl-oct-6-enyl) ester According to the procedure of Example 45, 2-[3-(2,6,6-trimethyl-cyclohex-1-enyl)-acryloyl]-malonic acid bis-(3,7-dimethyl-oct-6-enyl) ester was prepared from malonic acid bis-(3,7-dimethyl-oct-6-enyl) ester, 3-(2,6,6-trimethyl-cyclohex-1-enyl)-acryloyl chloride(Shimasaki et al., Chem. Pharm. Bull., 43 (1995) 1, 100–107) and sodium hydride.

EXAMPLE 48

2-Heptanoyl-malonic acid didec-9-enyl ester

According to the procedure of Example 45, 2-heptanoyl-malonic acid didec-9-enyl ester was prepared from malonic acid didec-9-enyl ester, heptanoyl chloride and sodium hydride.

EXAMPLE 49

2-Heptanoyl-malonic acid bis-(3,7-dimethyl-oct-6-enyl) ester

According to the procedure of Example 45, 2-heptanoyl-malonic acid bis-(3,7-dimethyl-oct-6-enyl) ester was prepared from malonic acid bis-(3,7-dimethyl-oct-6-enyl) ester, heptanoyl chloride and sodium hydride.

EXAMPLE 50

2,2-Diheptanoyl-malonic acid dihex-3-enyl ester

According to the procedure of Example 45, 2,2-diheptanoyl-malonic acid dihex-3-enyl ester was prepared from malonic acid dihex-3-enyl ester, heptanoyl chloride and sodium hydride.

EXAMPLE 51

2-(4-Methoxy-benzoyl)-malonic acid dihex-3-enyl ester

According to the procedure of Example 45, 2-(4-methoxy-benzoyl)-malonic acid dihex-3-enyl ester was prepared from malonic acid dihex-3-enyl ester, p-anisoyl chloride and sodium hydride.

EXAMPLE 52

2-Hex-3-enyloxycarbonyl-3-oxo-hexanedioic acid 6-(3,7-dimethyl-oct-6-enyl)ester 1-hex-3-enyl ester

According to the procedure of Example 45, 2-hex-3-enyloxycarbonyl-3-oxo-hexanedioic acid 6-(3,7-dimethyl-oct-6-enyl)ester 1-hex-3-enyl ester was prepared from malonic acid dihex-3-enyl ester, 3-chlorocarbonyl-propionic acid 3,7-dimethyl-oct-6-enyl ester and sodium hydride.

EXAMPLE 53

5-Heptyl-2-oxo-tetrahydro-furan-3-carboxylic acid

40 ml of 2,5-methoxymagnesium-methylcarbonate was added under nitrogen to 7.3 g 5-heptyl-dihydro-furan-2-one and heated to 140° C. for 6 hours. The reaction mixture then was poured into ice/hydrochloric acid and extracted with a mixture of tert-methyl butyl ether (MTBE) and diethyl ether. The organic layer was washed with water and brine, dried and evaporated to dryness. The residue then was dissolved in MTBE and extracted with saturated potassium hydrogen carbonate.

The aqueous layer was acidified and extracted with MTBE, the combined organic layers washed with brine, dryed and evaporated to dryness to yield 3.7 g of a solid, mp. 51–54° C.

NMR (CDCl$_3$) 6.1–5.5 (s, OH); 4.78–4.4 (m, 1H); 3.76–3.6 (m, 1H); 2.8–2.55 (m, 1H); 2.4–2.1 (m, 1H); 1.9–1.16 (m, 12H), 0.88 (s, 3H)

The compounds of the above examples are precursors for organoleptic compounds.

EXAMPLE 54

Test cloth was washed with a lipase-containing detergent to which one or more of the precursors of Examples 1–39, 45–52 had been added. Headspace analysis of the wet and dry laundry indicated the presence of the fragrances. The fragrance level was higher than when the test cloth was washed with a lipase-containing detergent to which one or more fragrances were added.

EXAMPLE 55

Test cloth was washed with a lipase-containing detergent and then a fabric softener, containing one or more of the precursors of Examples 1–39, 45–52 was added to the rinse cycle. Headspace analysis of the wet and dry laundry indicated the presence of the fragrances. The fragrance level was higher than when the test cloth was washed with a lipase-containing detergent and then a fabric softener, containing one or more fragrances, was added to the rinse cycle.

EXAMPLE 56

Axilla bacteria cultures containing 0.1% of one or more of the precursors of Examples 1–23 were incubated for 20 hours at 30° C. After filtration from the cells, the presence of the corresponding fragrance was in each case detected by headspace-GC techniques and/or the majority of an 18 member panel.

The same tests were carried out with inactivated cultures (85° C./20 min). The odour of the corresponding fragrance could not be detected after incubation, excluding therefore a hydrolysis by the medium or the culture.

EXAMPLE 57

The following set forth examples for the use of the compounds of the present invention in various products. The methods of forming the following compositions are well known to those skilled in the art. All formulations may contain additional ingredients known to those skilled in the art, e.g. colorants, opacifiers, buffers, antioxidants, vitamins, emulsifiers, UV absorbers, silicones and the like. All products can also be buffered to the desired pH. All values are % w/w. Delayed Release Fragrances stands in the following for compounds of Examples 1–39, 45–52.

a) Deo-colognes

| | | | | |
|---|---|---|---|---|
| Delayed Release Fragrances | 0.5 | 1.5 | 2.5 | 6.0 |
| Fragrance | 0.5 | 1.5 | 2.5 | 6.0 |
| Triclosan (Ciba Geigy) | 1.0 | — | 0.75 | 1.0 |
| Alcohol to | 100 | 100 | 100 | 100 | b) Deo-Sticks

| | |
|---|---|
| Antiperspirant | |
| Ethylene Glycol Monostearate | 7.0 |
| Shea butter | 3.0 |
| Neobee 1053 (PVO International) | 12.0 |
| Generol 122 (Henkel) | 5.0 |
| Kesscowax B (Akzo) | 17.0 |
| Dimethicone Dow Corning 345 | 35.0 |
| Aluminum Sesquichlorhydrate | 20.0 |
| Delayed Release Fragrances | 0.5 |
| Fragrance | 0.5 |
| Antiperspirant | |
| Steary Alcohol | 17.0 |
| Castor Wax | 3.0 |
| Talc | 5.0 |
| Aluminum Zirconium Tetrachlorhydrate | 20.0 |
| Delayed Release Fragrances | 1.0 |
| Fragrance | 1.0 |
| Dimethicone Dow 245 | to100.0 |
| Clear Deodorant Stick | |
| Witconol APM | 43.0 |
| Propylene Glycol | 20.0 |
| Alcohol 39C | 20.0 |
| Demin Water | 7.0 |
| Monamid 150ADD | 5.0 |
| Millithix 925 | 2.0 |
| Ottasept Extra | 0.5 |
| Delayed Release Fragrances | 0.75 |
| Fragrance | 0.75 |
| Deodorant Stick | |
| Propylene Glycol | 69.0 |
| Demin Water | 21.8 |
| Triclosan | 0.2 |
| Sodium Stearate | 8.0 |
| Delayed Release Fragrances | 0.5 |
| Fragrance | 0.5 |
| Alcohol free Deodorant Stick | |
| PPG-3 Myristyl Ether (Witconol APM) | 36.0 |
| Propylene Glycol | 36.0 |
| Demin Water | 19.0 |
| Triclosan | 0.25 |
| Sodium Stearate | 7.75 |
| Delayed Release Fragrances | 0.5 |
| Fragrance | 0.5 |
| Antiperspirant Aerosol | |
| Absolute Ethanol | 15.0 |
| Zirconium Aluminum Tetrachlorhydrate | 5.0 |

-continued

| | | |
|---|---|---|
| Bentone 38 | | 1.5 |
| Delayed Release Fragrances | | 0.75 |
| Fragrance | | 0.75 |
| S-31 Hydrocarbon propellant | | to 100.0 |
| Antiperspirant Pump | | |
| Demin Water | | 57.5 |
| Aluminum Sesquichlorhydrate | | 20.0 |
| Triton X-102 (Union Carbide) | | 2.0 |
| Dimethyl Isosorbide (ICI) | | 20.0 |
| Delayed Release Fragrances | | 0.25 |
| Fragrance | | 0.25 |
| Roll-On | | |
| Dimethicone DC 354 (Dow Corning) | | 69.0 |
| Bentone 38 | | 10.0 |
| Rezal 36 GP (Reheis Chem. Co.) | | 20.0 |
| Delayed Release Fragrances | | 0.5 |
| Fragrance | | 0.5 |

EXAMPLE 58 a) Fabric softener of the ester quat type (4×concentrate):

| INGREDIENTS | CHEMICAL NAME | % |
|---|---|---|
| PHASE A | | |
| DEIONISED WATER | | to 100.0 |
| MgCl$_2$ (saturated sol.) | Magnesium chloride | 1.0 |
| PHASE B | | |
| REWOQUAT WE 18 | di-(tallow carboxyethyl)hydroxy ethyl methylammonium methosulfate | 15.0 |
| GENAPOL O 100 | Ethoxylated fatty alcohol C16–C18 10EO | 2.0 |
| ANTIFOAM DB 31 | | 0.5 |
| PHASE C | | |
| ISOPROPYL ALCOHOL | | 3.0 |
| PRESERVATIVE | | Qs |
| PERFUME | | Qs |

Process

While stirring and heating to 65° C., mix part A, then part B preheated to 65° C. After cooling to room temperature, add part C. The pH value of the finished product is 2.60. Recommended level of perfume is 1.0%. Delayed release fragrances of Examples 1–39, 45–52 may be any part of this 1.0%.

b) Fabric softener of the ester quat type (1×concentrate):

| INGREDIENTS | CHEMICAL NAME | % |
|---|---|---|
| PHASE A | | |
| DEIONISED WATER | | to 100.0 |
| PHASE B | | |
| REWOQUAT WE 18 | Di-(tallow carboxyethyl)hydroxy ethyl methylammonium methosulfate | 6.0 |
| DOBANOL 25-9 | Ethoxylated fatty alcohol C12–C15 9EO | 0.50 |
| ANTIFOAM DB 31 | | 0.10 |
| PHASE C | | |

-continued

| INGREDIENTS | CHEMICAL NAME | % |
|---|---|---|
| MYACIDE BT 30 | 2-bromo-2-nitropropane 1,3 diol | 0.03 |
| PROXEL GXL | Benzisothiazolinone sodium salt | 0.02 |

Process

While stirring and heating to 65° C., mix part A, then part B preheated to 65° C. After cooling to room temperature, add part C. The pH value of the finished product is 3.50. Recommended level of perfume: 0.3%. Delayed release fragrances of Examples 1–39, 45–52 may be any part of this 0.3%.

EXAMPLE 59

A 1% solution of one or more of the products of Examples 1–39, 45–53 in ethanol was applied to cigarette papers to produce levels of 5–50,000 ppm of each flavourant. The paper was incorporated in cigarettes and, upon burning, released a fragrant odor.

In the above examples, the following components were used:

| | |
|---|---|
| Triclosan | 5-chloro-2-(2,4-dichloro-phenoxy)phenol |
| Neobee 1053 | glycerol tricaprate/caprylate |
| Generol 122 | soya sterol |
| Kesscowax B | cetyl alcohol and glycol polymer |
| Witconol APM | polypropylene glycol-3 myristyl ether |
| Monamid 150 ADD | cocoamide diethanolamine |
| Millithix 925 | dibenzylidene sorbitol |
| Ottasept Extra | quaternium 18 hectorite |
| Bentone 38 | quaternium 18 hectorite |
| Triton X-102 | octoxynol-13 |
| Dimethicone DC 354 | mixture of fully methylated linear siloxanepolymers end-blocked with trimethylsiloxy units |
| Rezal 36 GP | Aluminum zirconium tetra-chlorohydrexglycine |

While the invention has been described with respect to illustrative embodiments and modes of practice, it will be apparent to those skilled in the art that various modifications and improvements may be made without departing from the scope of the present invention.

What is claimed is:

1. A method of preparing organoleptic or antimicrobial compounds, comprising contacting a beta-keto ester of formula I:

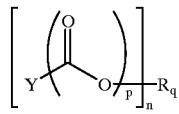

with a material selected from the group consisting of bacteria, an enzyme, and a material having an acidic or alkaline pH; elevating the temperature of the beta-keto ester of the above formula and exposing it to light, wherein
Y is the residue of an organoleptic ketone comprising 8 or more carbon atoms of the formula YH, R is the residue of a mono- or polyalcohol or phenol of the formula R—(OH)$_s$ with s≧1, p=1, 2, n=1 or 2, q 1, 2 and when p=n=1, either R is a nonfragrant monoalcohol having more than 3 carbon atoms or Y is a cyclic ketone as precursors for organoleptic and antimicrobial compounds.

2. The method according to claim 1, whereby the beta-ketoester is a fragrance precursor.

3. The method according to claim 1, whereby the beta-ketoester is a flavour precursor.

4. The method according to claim 1, whereby the beta-ketoester is a precursor for organoleptic masking agents.

5. The method according to claims 1, whereby the beta-ketoester is a precursor for antimicrobial agents.

6. The method according to claim 1, wherein the enzyme is taken from the group consisting of a protease and a lipase.

* * * * *